Figure 1:
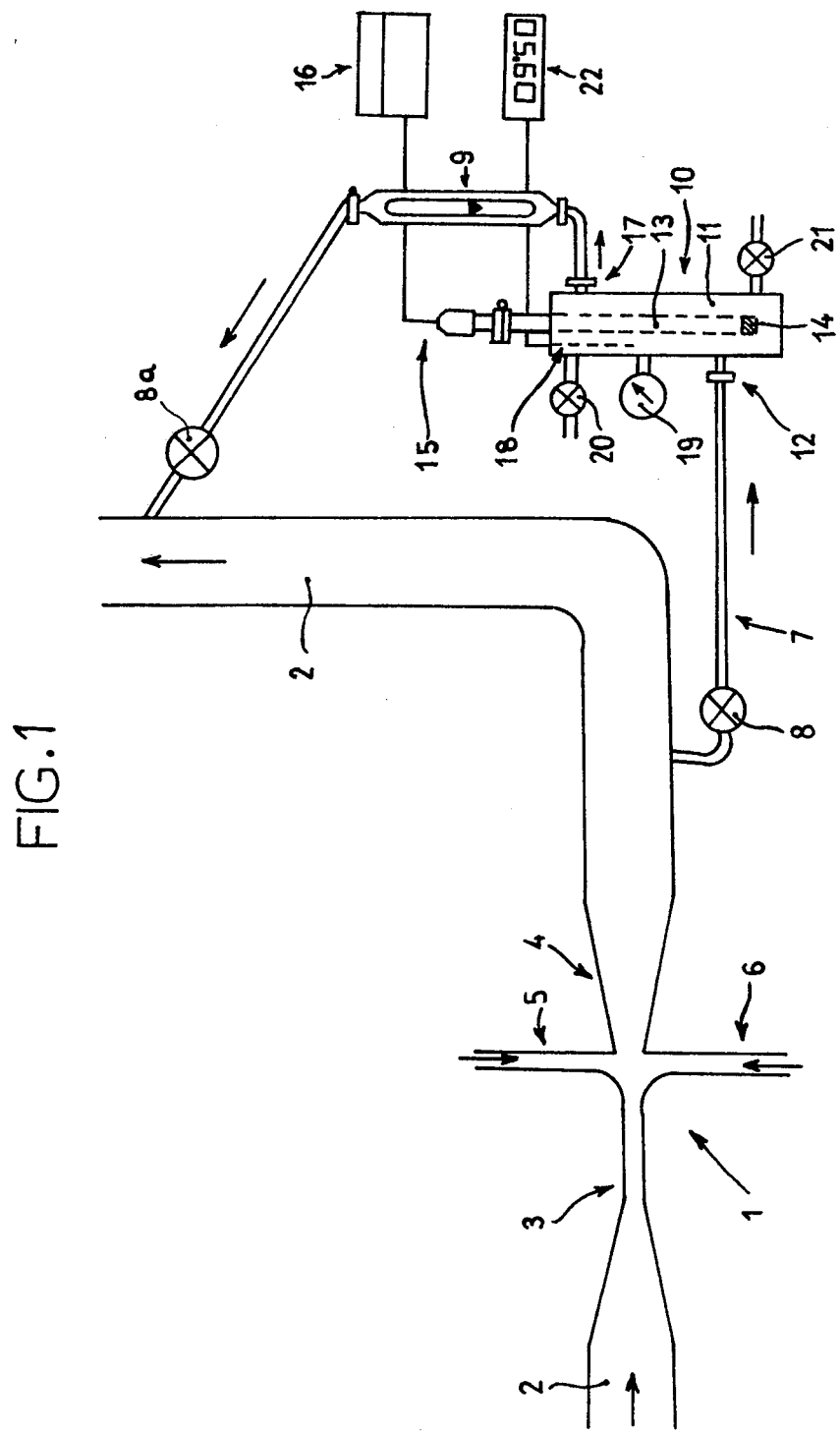

United States Patent [19]

Moll et al.

[11] 4,129,029

[45] Dec. 12, 1978

[54] DEVICE FOR MEASURING THE AMOUNT OF GAS DISSOLVED IN A LIQUID

[75] Inventors: Manfred Moll, Vandoeuvre; Christian D'Hardmemare; Nicolas Midoux, both of Nancy, all of France

[73] Assignee: Tepral, France

[21] Appl. No.: 766,195

[22] Filed: Feb. 7, 1977

[30] Foreign Application Priority Data

Dec. 22, 1976 [FR] France .................... 76 39349

[51] Int. Cl.$^2$ .................... G01N 27/46; G01N 33/14
[52] U.S. Cl. .................................................. 73/19
[58] Field of Search .................... 73/19, 23, 61 R; 204/1 Y, 195 R, 1 T; 23/230 R, 253 R, 232 R, 254 R

[56] References Cited

U.S. PATENT DOCUMENTS

| 2,736,190 | 2/1956 | Bockelmann et al. | 73/19 |
| 2,993,846 | 7/1961 | Tyler | 204/1 Y |
| 3,077,765 | 2/1963 | Dijkema | 73/19 |
| 3,673,853 | 7/1972 | Griswold et al. | 73/19 |
| 3,962,046 | 6/1976 | Morrison | 73/19 |

*Primary Examiner*—Stephen A. Kreitman
*Attorney, Agent, or Firm*—Robert E. Burns; Emmanuel J. Lobato; Bruce L. Adams

[57] ABSTRACT

Beer fermentation apparatus comprises a main pipe for transporting a water-entrained mixture of wort, yeast and gas to a fermentation tank. A measuring device is mounted in a by-pass circuit of the main pipe for measuring the amount of gas dissolved in the water, the device comprising a vertically disposed measuring chamber having an inlet at its lower end and an outlet at its upper end which are connected to upstream and downstream portions of the main pipe for flowing the mixture through the measuring chamber. The chamber inlet is located a sufficient distance above the lowermost end of the chamber so as to effect formation of a relatively stagnant flow region which is substantially free of gas bubbles in the measuring chamber beneath the level of the inlet during flow of the water-entrained mixture through the measuring chamber. A gas-sensitive element extends downwardly in the measuring chamber into the stagnant flow region for measuring the amount of gas dissolved in the mixture and due to the relative locations of the chamber inlet and outlet and the location of the gas-sensitive element, the gas bubbles and lighter mixture particles entrained in the water flow in the inlet upwardly through the measuring chamber and out the outlet while the heavier mixture particles entrained in the water tend to flow downwardly and settle in the stagnant flow region thereby minimizing erroneous measurements which would otherwise occur due to the presence of gas bubbles in the vicinity of the gas-sensitive element.

8 Claims, 2 Drawing Figures

DEVICE FOR MEASURING THE AMOUNT OF GAS DISSOLVED IN A LIQUID

This invention relates to a device for measuring the amount of a gas, in particular oxygen, dissolved in a liquid, and in particular for measuring the degree of oxygenation in a wort before or after its inoculation with yeast, that is before or during its fermentation phase, in the production of beer.

Up to the present time this procedure has been carried out in a continuous manner after the inoculation, or on a tapping or off-take, by inserting an electrode of the Clark measuring electrode type in the wort flow pipe. The procedure is carried out after the wort oxygenation phase, that is to say after the injection of a certain amount of oxygen or a gaseous mixture containing oxygen.

Experience shows that under these conditions there still exists a large and continuous flow of gas bubbles which cause random perturbations at the level of the measuring electrodes, producing quite false readings which are, of course, not a true indication of dissolved the actual amount of gas, in particular oxygen.

The number and variety of technical embodiments and size modifications for the pipe make it impossible to form a satisfactory mathematical model for the transfer of a gas in a liquid, especially in the case of a beer brewing plant. Corrections to the measurements using a mathematical approximation of the system are therefore not possible.

It has been observed that the dynamic pressure affects the measurements, this effect being greater the higher the pressure and the greater the number of bubbles. In order to restrict these perturbations it is thus necessary to reduce simultaneously the velocity of the fluid and the number of bubbles.

It has also not proved practical to carry out measurements in a local enlargement or widening in the pipe, since although such an enlargement reduces the dynamic pressure at the level of the measuring electrode, the large number of bubbles following the amount of air injected does not allow a stratified flow to take place and leads to the same measuring difficulties.

The present invention comprises a device for measuring the amount of gas dissolved in a liquid, the device being mounted in an off-take circuit from a main pipe which supplies wort to a fermentation tank, an upstream tapping being effected at the low point of the pipe. The device comprises a rectilinear closed body defining an internal measuring chamber having a side inlet branch in its lower or middle part, the chamber housing a central measuring electrode having a length such that a sensitive element for effecting the measurement is situated close to the bottom of the chamber and at a level lower than that of the said inlet. The chamber includes in its upper part an outlet branch, means for measuring the temperature, and various checking, safety and calibrating instruments.

By means of the invention it is possible to measure the degree of oxygenation of a wort by polarography under satisfactory measuring conditions within a device inserted in a circuit arranged as a tapping of the main flow pipe of the wort and which, by virtue of its location, the arrangement of its constituent elements, its internal technical structure and its volume, enables meaningful measurements to be made.

The device is placed in series in an off-take circuit and comprises a chamber having a low or central side inlet and an upper outlet, the chamber housing in its internal volume a central electrode whose measuring cell is at a level lower than that of the inlet, the device further comprising various safety and checking means.

The mounting of the device in an off-take circuit enables the number of bubbles at the level of the measuring cell to be reduced. Furthermore, the upstream tapping at the low point of the pipe further reduces the velocity and number of bubbles.

Finally, the device itself, without reducing the velocity of the fluid too much yet while preserving an advantageous response time, makes the disturbing effect of the bubbles negligible since their minimal number in the apparatus and their favoured path directly from the inlet to the outlet no longer causes them to flush the measuring cell.

Figure 2:
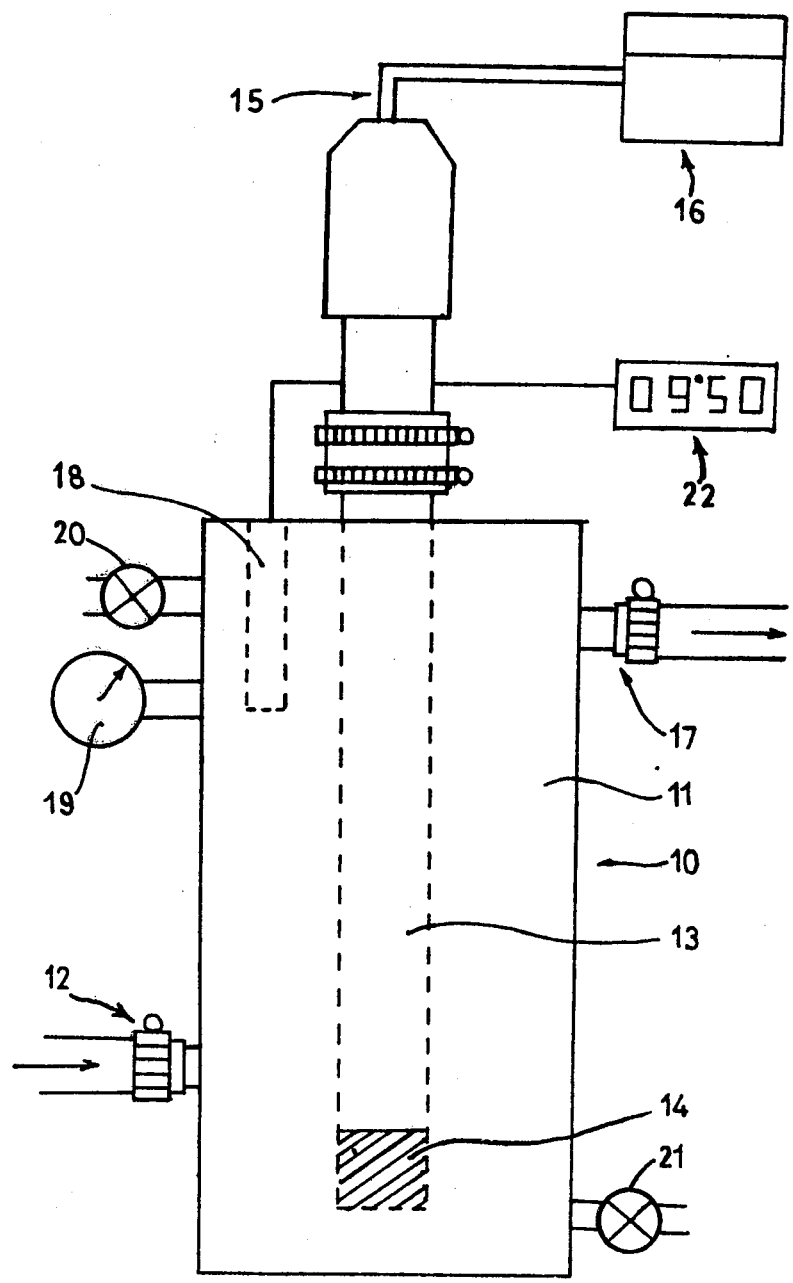

The invention will be further described, by way of example only, with reference to the accompanying drawings in which:

FIG. 1 is a general elevational view showing a device according to the invention and the circuit in which it is mounted; and FIG. 2 is an enlarged elevational view of the measuring device shown in FIG. 1.

The device is attached to the wort feed pipe of a fermentation tank after its inoculation and aeration, or to any other recirculation pipe conveying the wort during fermentation. In the arrangement shown, air and yeast are injected simultaneously into a mixing chamber 1 for the simultaneous inoculation and oxygenation of the wort. The chamber is placed in a wort supply pipe 2 and comprises a monoblock structure with a double nozzle arrangement comprising a converging nozzle 3 and then a diverging nozzle 4, and two lateral inlets 5 and 6 for air and yeast respectively, which enables a good dynamic mixing effect to be achieved by virtue of the venturi effect. The water-entrained mixture obtained after the inoculation and oxygenation is conveyed by the main pipe 2 to the fermentation tank.

The device itself is placed in a circuit 7 mounted as an off-take of the main pipe 2 supplying the wort mixture. Its upstream connection is effected by a tapping at the lower part of the pipe 2 and its downstream connection is effected after an angle joint. This low-level arrangement, in addition to the tapping, reduces the number of bubbles passing through the measuring device to a minimum. The off-take circuit 7 is isolated from the main pipe 2 by two valves 8 and 8a placed at the inlet and outlet respectively. A flow meter 9 having a direct reading or a digital display system is also provided in the off-take circuit, and is connected in series.

The device per se comprises an elongate, preferably rectilinear, closed body 10 defining an internal measuring chamber 11 having a single lateral inlet branch 12 in its lower or middle part, opposite a cylindrical measuring electrode 13 located centrally and occupying practically the whole length of the body 10 and terminating at its lower end in a gas sensitive element 14 of the cell type at least 1 cm from the bottom of the chamber.

It is estimated that the distance between the inlet and the cell should not be less than 2 cm in order to obtain a good measurement independent of the effect of the bubbles, and an adequate response time.

The measuring electrode 13 is secured to the upper part of the body 10 and emerges from the latter via an end provided with electrical connecting leads 15 which transmit the signal or measurement current to a processing and display circuit box 16.

The body 10 contains, in the vicinity of its upper part and in the same plane as the inlet 12, an outlet branch 17 directly connected to the flow meter 9. Experiments show that the distance between the inlet and outlet branches should exceed 2 cm.

The chamber 11 also contains in its upper part, opposite the outlet 17, a temperature detector in the form of a glove finger 18 for detecting the temperature, and also various checking, safety, calibrating and operating devices such as a manometer 19 and upper and lower air stopcocks 20 and 21 respectively. The two air stopcocks enable the sampling device to be recalibrated at any instant without having to remove the device from the arrangement. The temperature detector is connected to an indicator unit 22 and, as mentioned above, the electrode is connected to a box 16 for processing the display information.

By virtue of the position of the sensitive cell 14 and the inlet branch 12 situated in the vicinity of the base of the chamber 11, and also the position of the outlet branch 17, a low turbulence zone or stagnant flow region which is substantially free from bubbles is formed beneath the inlet at the level of the measuring cell. Furthermore, the off-take circuit 7 is closed through the device by a direct path going from the inlet branch 12 to the outlet branch 17.

Thus, by means of this device, it becomes possible to carry out meaningful and stable measurements of constant accuracy without the random disturbances in the direct measurement systems previously employed. Furthermore, if the temperature is known it is a simple matter to determine the actual value of the amount of dissolved oxygen.

What we claim is:

1. In combination with beer fermentation apparatus having a main pipe for transporting a water-entrained mixture of wort, yeast and gas to a fermentation tank: a measuring device for measuring the amount of gas dissolved in the water comprising; means defining an elongated measuring chamber having upper and lower ends and having means defining an inlet for charging the water-entrained mixture into said measuring chamber and an outlet for discharging the water-entrained mixture from said measuring chamber, said outlet being located in the vicinity of said chamber upper end and said inlet being located a sufficient distance above said chamber lower end and coacting with said outlet to effect formation of a relatively stagnant flow region substantially free of gas bubbles in said measuring chamber beneath the level of said inlet during flow of the water-entrained mixture through said measuring chamber; conduit means connecting said measuring chamber inlet to an upstream portion of said main pipe and connecting said measuring chamber outlet to a downstream portion of said main pipe to divert flow of a part of the water-entrained mixture from said main pipe through said measuring chamber and then back to said main pipe such that the gas bubbles and lighter mixture particles entrained in the water flow in said inlet upwardly through said measuring chamber and out said outlet while the heavier mixture particles entrained in the water tend to flow downwardly and settle in the stagnant flow region; gas measuring means extending downwardly into said measuring chamber towards said lower end and including a gas-sensitive element disposed in the stagnant flow region of said measuring chamber which is substantially free of gas bubbles for measuring the amount of gas dissolved in the water-entrained mixture and providing a corresponding output signal indicative of the dissolved gas content.

2. Apparatus according to claim 1; wherein the endmost tip of said gas-sensitive element extends at least 1 cm from the chamber lower end.

3. Apparatus according to claim 2; wherein the endmost tip of said gas-sensitive element extends more than 2 cm beneath the level of said inlet.

4. Apparatus according to claim 1; wherein said upstream portion of said main pipe extends generally horizontally and said downstream portion of said main pipe extends generally vertically thereby reducing the number and velocity of gas bubbles in that part of the water-entrained mixture diverted through said measuring chamber.

5. Apparatus according to claim 1; further including means for measuring the temperature of the water-entrained mixture flowing through said measuring chamber.

6. Apparatus according to claim 1; further including means for measuring the pressure of the water-entrained mixture flowing through said measuring chamber.

7. Apparatus according to claim 1; further including calibrating means for enabling calibration of the measuring device while connected to said main pipe.

8. Apparatus according to claim 7; wherein said calibrating means includes two air stopcocks connected respectively at the upper and lower end portions of said measuring chamber.

* * * * *